United States Patent
Wegrzyn, III et al.

(10) Patent No.: US 10,194,971 B2
(45) Date of Patent: Feb. 5, 2019

(54) ELECTROSURGICAL GENERATOR

(71) Applicant: COSMAN MEDICAL, INC., Burlington, MA (US)

(72) Inventors: Thomas John Wegrzyn, III, Cambridge, MA (US); Eric Cosman, Jr., Belmont, MA (US)

(73) Assignee: COSMAN MEDICAL, INC., Burlington, MA (US)

( * ) Notice: Subject to any disclaimer, the term of this patent is extended or adjusted under 35 U.S.C. 154(b) by 1153 days.

(21) Appl. No.: 14/499,013

(22) Filed: Sep. 26, 2014

(65) Prior Publication Data

US 2018/0036060 A1 Feb. 8, 2018

(51) Int. Cl.
*A61B 18/14* (2006.01)
*A61B 18/08* (2006.01)
*A61B 18/00* (2006.01)

(52) U.S. Cl.
CPC ........ *A61B 18/082* (2013.01); *A61B 18/1477* (2013.01); *A61B 2018/00107* (2013.01); *A61B 2018/00136* (2013.01); *A61B 2018/00791* (2013.01); *A61B 2218/002* (2013.01)

(58) Field of Classification Search
CPC .............. A61B 18/1477; A61B 18/148; A61B 18/1487; A61B 18/082; A61B 2018/00541; A61B 2018/00529; A61B 2018/00577; A61B 2018/00011; A61B 2018/00029; A61B 2018/00339; A61B 2018/00351; A61B 2018/00446; A61B 2018/00511; A61B 2018/00565; A61B 2018/1495; A61B 2018/1425; A61B 2018/00607; A61B 2018/1475
See application file for complete search history.

(56) References Cited

U.S. PATENT DOCUMENTS

| | | | |
|---|---|---|---|
| 3,532,095 A * | 10/1970 | Miller | A61B 18/1402 606/45 |
| 4,411,266 A * | 10/1983 | Cosman | A61B 18/14 600/549 |
| 4,565,200 A | 1/1986 | Cosman | |
| 4,566,454 A | 1/1986 | Mehl et al. | |
| 4,597,379 A | 7/1986 | Kihn et al. | |
| 4,727,874 A | 3/1988 | Bowers et al. | |
| 4,807,620 A | 2/1989 | Strul et al. | |
| 5,433,739 A | 7/1995 | Sluijter et al. | |
| 5,571,147 A | 11/1996 | Sluijter et al. | |
| 5,769,847 A | 6/1998 | Panescu et al. | |
| 5,951,546 A | 9/1999 | Lorentzen | |
| 5,983,141 A | 11/1999 | Sluijter et al. | |
| 6,104,959 A | 8/2000 | Spertell | |

(Continued)

FOREIGN PATENT DOCUMENTS

| WO | WO 99/40859 | 8/1999 |
|---|---|---|
| WO | WO 99/40860 | 8/1999 |
| WO | WO 00/59394 | 10/2000 |

OTHER PUBLICATIONS

Cosman et al. "Theoretical Aspects of Radiofrequency Lesions in the Dorsal Root Entry Zone," *Neurosurgery*, vol. 15, No. 6, p. 945-950 (1984).

*Primary Examiner* — Michael Peffley

(57) ABSTRACT

A system and method for applying energy, particularly high-frequency (HF) energy, such as radiofrequency (RF) electrical energy, to a living body can include a cannula hub.

14 Claims, 6 Drawing Sheets

(56) References Cited

U.S. PATENT DOCUMENTS

| | | |
|---|---|---|
| 6,161,048 A | 12/2000 | Sluijter et al. |
| 6,246,912 B1 | 6/2001 | Sluijter et al. |
| 6,259,952 B1 | 7/2001 | Sluijter et al. |
| 6,301,506 B1 | 10/2001 | Den Boer et al. |
| 6,321,120 B1 | 11/2001 | Surbeck et al. |
| 6,397,106 B1 | 5/2002 | DeBrouse |
| 6,402,739 B1 | 6/2002 | Neev |
| 6,428,537 B1 | 8/2002 | Swanson et al. |
| 6,440,127 B2 | 8/2002 | McGovern et al. |
| 6,447,505 B2 | 9/2002 | McGovern et al. |
| 6,482,204 B1 | 11/2002 | Lax et al. |
| 6,517,534 B1 | 2/2003 | McGovern et al. |
| 6,530,922 B2 | 3/2003 | Cosman et al. |
| 6,692,493 B2 | 2/2004 | McGovern et al. |
| 6,743,226 B2 | 6/2004 | Cosman et al. |
| 6,843,789 B2 | 1/2005 | Goble |
| 6,853,864 B2 | 2/2005 | Litovitz |
| 6,869,430 B2 | 3/2005 | Balbierz et al. |
| 6,936,048 B2 * | 8/2005 | Hurst ............... A61B 18/1477 600/439 |
| 7,522,953 B2 | 4/2009 | Kaula et al. |
| 7,553,309 B2 | 6/2009 | Buysse et al. |
| 7,574,257 B2 | 8/2009 | Rittman, III |
| 7,862,563 B1 * | 1/2011 | Cosman ............. A61B 18/1477 606/41 |
| 7,976,542 B1 * | 7/2011 | Cosman ................ A61B 6/504 606/41 |
| 2002/0156472 A1 | 10/2002 | Lee et al. |
| 2002/0165531 A1 | 11/2002 | Goble |
| 2003/0032951 A1 | 2/2003 | Rittman et al. |
| 2003/0212390 A1 | 11/2003 | Chen et al. |
| 2006/0178666 A1 * | 8/2006 | Cosman ............... A61B 18/148 606/41 |
| 2007/0032835 A1 | 2/2007 | Rittman |
| 2008/0262490 A1 | 10/2008 | Williams |
| 2014/0081260 A1 * | 3/2014 | Cosman, Jr. ........ A61B 18/1477 606/41 |

* cited by examiner

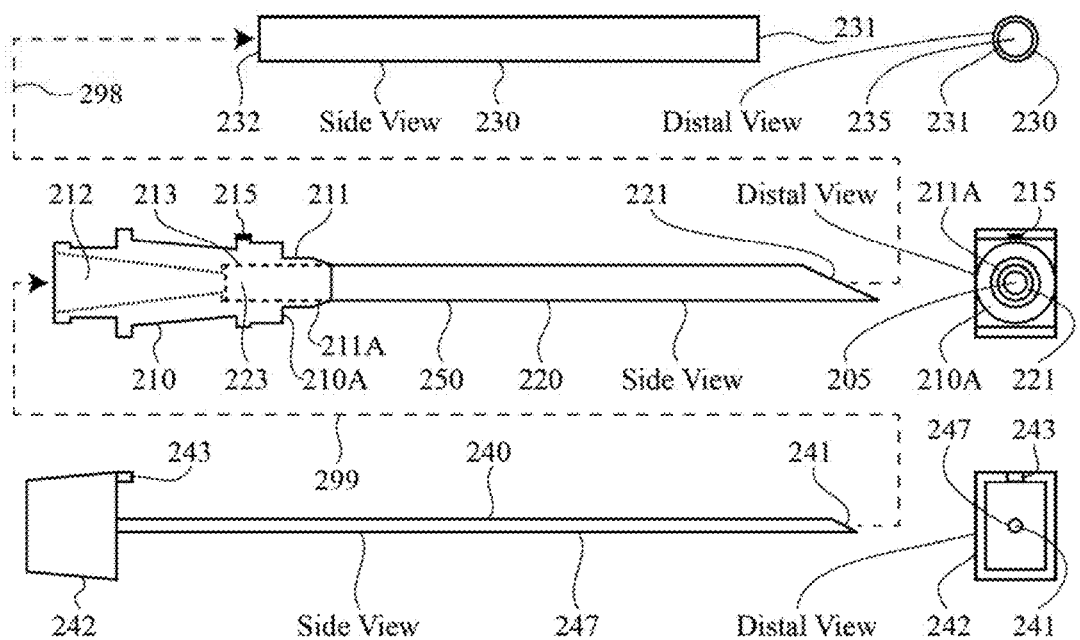
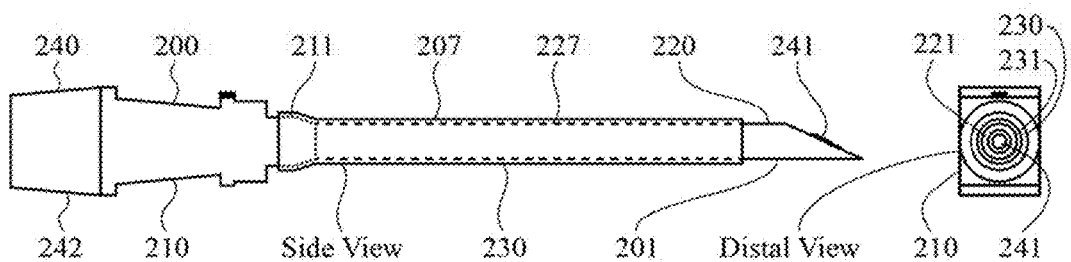
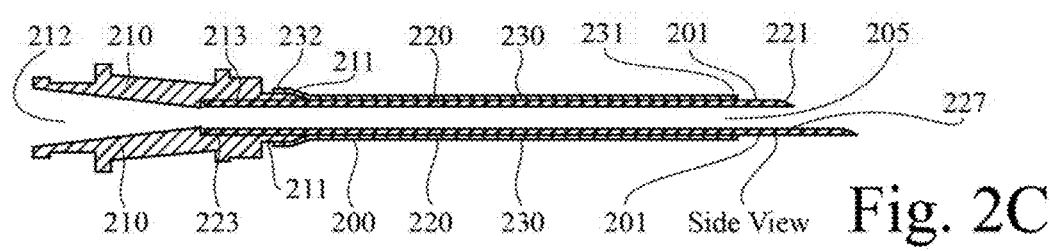
Fig. 2A
Fig. 2B
Fig. 2C

ELECTROSURGICAL GENERATOR

TECHNICAL FIELD

This invention relates generally to the advances in medical systems and procedures for prolonging and improving human life. The present invention also relates generally systems and methods pertaining to coated medical probes. The present invention also relates generally to a system and method for applying energy, particularly high-frequency (HF) energy, such as radiofrequency (RF) electrical energy, to a living body. The present invention also relates generally to a system and method for apply energy for the purpose of tissue ablation.

BACKGROUND

The use of radiofrequency (RF) generators and electrodes to be applied to tissue for pain relief or functional modification is well known. For example, the RFG-3C plus RF lesion generator of Radionics, Inc., Burlington, Massachusetts and its associated electrodes enable electrode placement near target tissue and the heating of the target tissue by RF power dissipation of the RF signal output in the target tissue. For example, the G4 generator of Cosman Medical, Inc., Burlington, Mass. and its associated electrodes (such as the Cosman CSK electrode), cannula (such as the Cosman CC and RFK cannulae), and ground pads (such as the Cosman DGP-PM) enable electrode placement near target tissue and heating of the target tissue by RF power dissipation of the RF signal output in the target tissue. Temperature monitoring of the target tissue by a temperature sensor in the electrode can control the process. Heat lesions with target tissue temperatures of 60 to 95 degrees Celsius are common. Tissue dies and nerves are severed by sustained heating above about 45 degrees Celsius, so this process produces the RF heat lesion. RF generator output is also applied using a pulsed RF method, whereby RF output is applied to tissue intermittently such that tissue is exposed to high electrical fields and average tissue temperature are lower, for example 42 degrees Celsius or less.

RF generators and electrodes are used to treat pain, cancer, and other diseases. Related information is given in the paper by Cosman E R and Cosman B J, "Methods of Making Nervous System Lesions", in Wilkins R H, Rengachary S (eds.); Neurosurgery, New York, McGraw Hill, Vol. 3, 2490-2498; and is hereby incorporated by reference in its entirety. Related information is given in the book chapter by Cosman E R Sr and Cosman E R Jr. entitled "Radiofrequency Lesions.", in Andres M. Lozano, Philip L. Gildenberg, and Ronald R. Tasker, eds., Textbook of Stereotactic and Functional Neurosurgery (2nd Edition), 2009, and is hereby incorporated by reference in its entirety. A research paper by E. R. Cosman, et al., entitled "Theoretical Aspects of Radiofrequency Lesions and the Dorsal Root Entry Zone," by Cosman, E. R., et al., *Neurosurg* 1984;15: 945-950, describes various techniques associated with radio frequency lesions and is hereby incorporated by reference herein in its entirety. Research papers by S. N. Goldberg, et al., entitled "Tissue Ablation with Radio Frequency: Effect of Probe Size, Gauge, Duration, and Temperature on Lesion Volume," *Acad. Radiol.*, Vol. 2, pp. 399-404 (1995), and "Thermal Ablation Therapy for Focal Malignancy," *AJR*, Vol. 174, pp. 323-331 (1999), described techniques and considerations relating to tissue ablation with radio frequency energy and are hereby incorporated by reference herein in its entirety. For a given electrode temperature, size of electrode, and time of heating, you can predict reliably ablation size as described in the papers entitled "Theoretical Aspects of Radiofrequency Lesions and the Dorsal Root Entry Zone," by Cosman, E. R., et al., *Neurosurg* 15:945-950, 1984, and "Bipolar Radiofrequency Lesion Geometry: Implications for Palisade Treatment of Sacroiliac Joint Pain." by E. R. Cosman Jr and C. D. Gonzalez, Pain Practice 2011; 11(1): 3-22 (hereinafter "Cosman and Gonzalez"), which are herein incorporated by reference in their entireties.

The use of high frequency (HF) electrodes for heat ablation treatment in the destruction of tumors is well known. One example is the destruction of cancerous tumors of the kidney using radio frequency (RF) heat ablation. A paper by D. W. Gervais, et al., entitled "Radio Frequency Ablation of Renal Cell Carcinoma: Early Clinical Experience," Radiology, Vol. 217, No. 2, pp. 665-672 (2000), describes using a rigid tissue perforating and penetrating electrode that has a sharpened tip to self-penetrate the skin and tissue of the patient. This paper is hereby incorporated by reference herein in its entirety. A paper by Luigi Solbiati et al. entitled "Hepatic Metastases: Percutaneous Radiofrequency Ablation with Cool-Tip Electrodes," Radiology 1997, vol. 205, no. 2, pp. 367-373 describes various techniques and considerations relating to tissue ablation with RF electrodes which are internally-cooled by circulating fluid, and is incorporated herein by reference. A paper by Rosenthal et al entitled "Percutaneous Radiofrequency Treatment of Osteoid Osteoma," Seminars in Musculoskeletal Radiology, Vol. 1, No. 2, 1997 reports the treatment of a primary benign bone tumor and the management of concomitant pain using a percutaneously placed radiofrequency electrode, and is incorporated herein by reference. United States patents by E. R. Cosman and W. J. Rittman, III, entitled "Cool-Tip Electrode Thermal Surgery System," U.S. Pat. No. 6,506, 189 B1, date of patent Jan. 14, 2003, and "Cluster Ablation Electrode System," U.S. Pat. No. 6,530,922 B1, date of patent Mar. 11, 2003, described systems and method related to tissue ablation with radiofrequency energy and electrodes and are hereby incorporated by reference herein in their entirety. Another example of probes for high-frequency tissue ablation includes microwave (MW) antennae. Another example of probes for tissue ablation are irreversible-electroporation (IRE) probes. Another example of probes for tissue ablation are cryogenic ablation probes.

Each Cosman CC cannula and RFK cannula, manufactured by Cosman Medical, Inc. in Burlington, Mass., includes a pointed metal shaft that is insulated except for an uninsulated electrode tip. The CC cannula has a straight shaft. The RFK cannula has a curved shaft; one advantage of a curved shaft is that it can facilitate maneuvering of the cannula's tip within tissue. Each cannula includes a removable stylet rod that can occlude the inner lumen of the cannula's shaft (which can, for example, facilitate insert of the cannula into solid tissue) and can be removed to allow for injection of fluids or insertion of instruments, like an electrode. Each cannula has a hub at its proximal end, the hub sized for manual manipulation of the cannula and having a luer port to accommodate an injection syringe or a thermocouple (TC) electrode, for example the Cosman CSK electrode, Cosman TCD electrode, and Cosman TCN electrode, that can deliver electrical signal output, such as RF voltage or stimulation, to the uninsulated cannula active tip and that can measure the temperature at the cannula active tip. The Cosman CSK and TCD electrodes have a shaft that is stainless steel. The Cosman TCN electrode has a shaft that is Nitinol. One CC or RFK cannula works with one CSK, TCD, or TCN electrode a two-piece RF electrode system configured for ablation of bodily tissue with temperature control. The Cosman CU electrode is an example of a one-piece RF electrode system wherein the electrode shaft has a tissue-piecing tip, insulation over the proximal shaft to produce an active electrode tip at the shaft distal end, a thermocouple temperature sensor with the active electrode tip, an injection port, a connection to an RF generator, and a lumen within the shaft to provide for fluid injection. The Cosman CR electrode is an example of a one-piece, tissue-piercing, radiofrequency, injection electrode that does not include a temperature sensor. The Cosman CP electrode is an example of a one-piece stimulation electrode system wherein the electrode shaft has a tissue-piecing tip, insulation over the proximal shaft to produce an active electrode tip at the shaft distal end, an injection port, a connection to an nerve-stimulation signal generator (which can be included in an RF generator, in some embodiments), and a lumen within the shaft to provide for fluid injection. Related information is given in Cosman Medical brochure "Four Electrode RF Generator", brochure number 11682 rev A, copyright 2010, Cosman Medical, Inc., and is hereby incorporated by reference herein in its entirety.

It is desirable that an RF probe (which includes both unitized RF electrodes, and RF cannula that work with separate electrodes), a nerve-stimulation injection needle, a muscle-stimulation needle, a medical electrode, or another type of electrical medical probe having an electrically-insulated shaft and electrically-insulated hub are constructed such that there is no gap in the electrical insulation at the interface between the hub and the shaft. One reason that the lack of a hub-to-shaft insulation gap is desirable is the probe shaft can be inserted into tissue all the way up to the probe hub without risk that electrical current will flow from a conductive gap between the hub and shaft and thereby unintentionally heat, burn, stimulate, measure, or otherwise affect tissue at that location (such as skin in the case of percutaneously placed RF cannula, RF electrode, active electrode probe, or measurement electrode probe). In a first example in the prior art, avoiding an electrical-insulation gap at the hub-to-shaft interface of an RF probe is accomplished by first applying electrical insulation (such as by heating shrinking plastic heat shrink tubing over the shaft, or by spraying, painting, or dipping fluid insulation onto the shaft) over the metallic probe shaft, and then attaching the hub to shaft such that the hub covers both the shaft and the insulation (for example, by gluing the hub to the insulated shaft, or insert-molding the hub over the insulated shaft) such that there is no uninsulated gap between the hub and shaft that could contact tissue. One disadvantage of the said first example in the prior art, is that the insulation is attached to the shaft before the hub is attached to the shaft. Another disadvantage of the first example in the prior art, is the process of attaching the hub to the shaft must be designed to avoid damaging the insulation; for example, the process must have thermal, chemical, and physical characteristics that are not degrading to the insulation. In a second example in the prior art, avoiding an electrical-insulation gap at the hub-to-shaft interface of an RF probe is accomplished by first attaching the hub to the metallic shaft (for example by gluing or insert-molding), then applying the insulation to the shaft (such as by heating shrinking plastic heat shrink tubing over the shaft, or by spraying, painting, or dipping fluid insulation onto the shaft), and then covering any part of the metallic shaft that is not covered by the hub or the insulation at the hub-to-shaft interface (for example, applying glue between the shaft and hub, or precisely sliding the insulation along the shaft up to the hub). In the case where the electrical insulation is heat shrink tubing, application of the tubing to the shaft by heating it can cause the tubing to shrink both radially and longitudinally, and the longitudinal shrinkage of the insulation can leave part of the metallic shaft exposed unless the insulation is fixtured during shrinking or repositioned after shrinking. In the case where electrical insulation is applied to the shaft by spraying, painting or dipping inaccuracies in the process can lead to parts where the metallic shaft is exposed. One disadvantage of the said second example in the prior art is that an additional operation is performed to cover any gap in the insulation at the hub-to-shaft interface. Another disadvantage of the second example in the prior art is that greater precision, and often greater time, is required in the application of insulation to shaft to avoid gaps in the insulation at the hub-to-shaft interface.

The present invention overcomes the stated disadvantages and other limitations of the prior art.

SUMMARY OF THE INVENTION

In one aspect, the present invention relates to the geometry of the hub of a probe, such as a needle, cannula, electrode, active electrode, measurement electrode, stimulation electrode, nerve-stimulation electrode, RF cannula, RF electrode, MW ablation antenna, IRE electrode, or tissue ablation probe. In one aspect, the present invention relates to the construction of a coated probe, such as a needle, cannula, electrode, RF cannula, RF electrode, or tissue ablation probe. In one aspect, the present invention relates to methods for coating a probe, such as a needle, cannula, electrode, active electrode, measurement electrode, stimulation electrode, nerve-stimulation electrode, RF cannula, RF electrode, MW ablation antenna, IRE electrode, or tissue ablation probe.

In some applications, it is desirable to have a continuous, unbroken coating over a length of the shaft of a medical probe and over the junction between the shaft and the hub of the probe. In some examples, the coating can provide desired surface properties, such as low friction or non-reactiveness. In some applications, it is desirable for the junction between the hub and the shaft of a medical probe to be coated and smooth, without discontinuities or crevices in which material could be inadvertently captured. For example, the coating can be used to isolated shaft materials from the tissue traversed by shaft during placement of the shaft within tissue. For example, the coating can provide a low-friction interface between the shaft and the tissue. Such applications are also in the scope of the present invention.

In one aspect, the present invention relates to a probe including a needle and a coating, the needle including an elongated shaft and a hub, the shaft having a proximal end and a distal end, the distal end of the shaft being configured for insertion into bodily tissue, the hub being fixedly attached to the proximal end of the shaft and including a narrow recess between the hub and the shaft, the coating covering at least a part of the shaft, and one end of the coating being positioned within the recess.

In one aspect, the present invention relates to a probe including a needle and heat-shrink tubing, the needle including an elongated shaft and a hub, the shaft having a proximal end and a distal end, the distal end of the shaft being configured for insertion into bodily tissue, the hub being fixedly attached to the proximal end of the shaft and including a narrow recess between the hub and the shaft, the heat-shrink tubing covering at least a part of the shaft, and one end of the heat-shrink tubing being positioned within the recess.

In one aspect, the present invention relates to an RF cannula constructed by sliding heat-shrinkable and electrically-insulative tubing along the cannula shaft and into a recess in the cannula hub, and applying heat to shrink the tubing onto the shaft such that one end of the heat-shrink tubing remains in the recess.

In one aspect, the present invention relates to a unitized, tissue-penetrating RF electrode constructed by sliding heat-shrinkable and electrically-insulative tubing along the electrode shaft and into a recess in the electrode hub, and applying heat to shrink the tubing onto the shaft such that one end of the heat-shrink tubing remains in the recess.

In one aspect, the present invention relates to a probe including a needle and a coating, the needle including an elongated shaft and a hub, the shaft having a proximal end and a distal end, the distal end of the shaft being configured for insertion into bodily tissue, the hub being fixedly attached to the proximal end of the shaft and including a thin protrusion covering a portion of the proximal end of the shaft, the coating covering both at least a part of the shaft and at least a part of the protrusion.

In one aspect, the present invention relates to a probe including a needle and heat-shrink tubing, the needle including an elongated shaft and a hub, the shaft having a proximal end and a distal end, the distal end of the shaft being configured for insertion into bodily tissue, the hub being fixedly attached to the proximal end of the shaft and including a thin protrusion covering a portion of the proximal end of the shaft, the heat-shrink tubing covering both at least a part of the shaft and at least a part of the protrusion.

In one aspect, the present invention relates to an RF cannula constructed by sliding heat-shrinkable and electrically-insulative tubing along the cannula shaft and over a protrusion of the cannula hub over the cannula shaft, and applying heat to shrink the tubing onto the shaft such that one end of the heat-shrink tubing remains over the protrusion.

In one aspect, the present invention relates to a unitized, tissue-penetrating RF electrode constructed by sliding heat-shrinkable and electrically-insulative tubing along the electrode shaft and over a protrusion of the electrode hub over the cannula shaft, and applying heat to shrink the tubing onto the shaft such that one end of the heat-shrink tubing remains over the protrusion.

In one aspect, the present invention relates to a method for coating a probe comprising: assembling a shaft and hub, and applying coating over the shaft and within a narrow recess in the hub at the junction between the hub and the shaft.

In one aspect, the present invention relates to a method for coating a probe comprising: assembling a shaft and hub, sliding heat-shrink tubing over the shaft and into a narrow recess in the hub at the junction between the hub and the shaft, and applying heat to the tubing to shrink the tubing onto the shaft so that a portion of the tubing remains within the recess.

In one aspect, the present invention relates to a method for insulating an RF cannula comprising: assembling a shaft and hub, sliding heat-shrink tubing over the shaft and into a narrow recess in the hub at the junction between the hub and the shaft, and applying heat to the tubing to shrink the tubing onto the shaft so that a portion of the tubing remains within the recess.

In one aspect, the present invention relates to a method for insulating an tissue-penetrating RF electrode comprising: assembling a shaft and hub, sliding heat-shrink tubing over the shaft and into a narrow recess in the hub at the junction between the hub and the shaft, and applying heat to the tubing to shrink the tubing onto the shaft so that a portion of the tubing remains within the recess.

In one aspect, the present invention relates to a method for coating a probe comprising: assembling a shaft and hub, and applying coating over the shaft and over a thin protrusion of the hub over the shaft at the junction between the hub and the shaft.

In one aspect, the present invention relates to a method for coating a probe comprising: assembling a shaft and hub, sliding heat-shrink tubing over the shaft and over a thin protrusion of the hub over the shaft at the junction between the hub and the shaft, and applying heat to the tubing to shrink the tubing onto the shaft so that a portion of the tubing remains over the protrusion.

In one aspect, the present invention relates to a method for insulating an RF cannula comprising: assembling a shaft and hub, sliding heat-shrink tubing over the shaft and over a thin protrusion of the hub over the shaft at the junction between the hub and the shaft, and applying heat to the tubing to shrink the tubing onto the shaft so that a portion of the tubing remains over the protrusion.

In one aspect, the present invention relates to a method for insulating an tissue-penetrating RF electrode comprising: assembling a shaft and hub, sliding heat-shrink tubing over the shaft and over a thin protrusion of the hub over the shaft at the junction between the hub and the shaft, and applying heat to the tubing to shrink the tubing onto the shaft so that a portion of the tubing remains over the protrusion.

In one aspect, the present invention is directed towards the problem of efficiently and completely coating the shaft of a medical probe. In one aspect, the present invention is directed toward the problem of continuously coating the shaft of a probe having a hub configured for manipulation of the probe in bodily tissue and/or injection of fluids into the hub and through the probe shaft. In one aspect, the present invention is directed to ensuring continuous coating of a probe shaft including at the junction between the probe hub and the probe shaft. In one aspect, the present invention is directed toward the problem of efficiently electrically-insulating the entirety of a shaft of an electrode having a hub configured for manipulation of the electrode in bodily tissue and/or injection of fluids into the hub and through the electrode shaft.

In one aspect, the present invention is directed toward the problem of applying electrical insulation to the shaft of a radiofrequency cannula. In one aspect, the present invention is directed toward the problem of applying electrical insulation to the shaft of a radiofrequency electrode. In one aspect, the present invention is directed toward the problem of applying electrical insulation to the shaft of a radiofrequency ablation probe.

In one aspect, the present invention is directed toward the problem of preventing leakage current along the shaft of probe electrode except at designated electrode contacts. In one aspect, the present invention is directed toward the problem of preventing leakage current at the junction between the shaft and hub of an electrode probe. In one aspect, the present invention is directed toward the problem of preventing a superficial burn at the site of insertion of a radiofrequency ablation probe. In one aspect, the present invention is directed toward the problem of preventing skin burns in the use of radiofrequency ablation probes, such as RF cannulae and RF electrodes. In one aspect, the present invention is directed toward the problem of preventing skin burns in the use of a radiofrequency ablation probe due to a gap in the shaft electrical insulation at the junction between the probe shaft and the probe hub, if the probe is inserted into bodily tissue percutaneously such that the probe shaft is completely inserted into the body so that the hub contacts the skin surface.

In one aspect, the present invention relates to the construction of a medical probe having a hub, a shaft, and a shaft coating. In one aspect, the present invention relates to the construction of a medical cannula having a shaft coating. In one aspect, the present invention relates to the construction of an RF cannula having shaft insulation. In one aspect, the present invention relates to the construction of a medical electrode having shaft insulation. In one aspect, the present invention relates to the construction of an RF electrode having shaft insulation.

In one aspect, the present invention relates to the geometry of the hub of a medical probe. In one aspect, the present invention relates to the geometry of the hub of a medical cannula. In one aspect, the present invention relates to the geometry of the hub of an ablation probe. In one aspect, the present invention relates to the geometry of the hub of an RF cannula. In one aspect, the present invention relates to the geometry of the hub of a medical electrode. In one aspect, the present invention relates to the geometry of the hub of an RF electrode.

In one aspect, the present invention relates to a method for coating a medical probe having a hub, a shaft, and a shaft coating. In one aspect, the present invention relates to a method for coating a medical cannula. In one aspect, the present invention relates to a method for insulating the shaft of an RF cannula. In one aspect, the present invention relates to a method for insulating the shaft of an RF electrode. In one aspect, the present invention relates to a method for insulating the shaft of a medical electrode.

The invention relates to probes that can be used in one or more organs in the body, including without limitation organs in the following list: brain, spine, liver, lung, bone, vertebral bone, kidney, abdominal structures, nerves, peripheral nerve, central nervous system, peripheral nervous system, pancreas. The invention relates to probes configured for use for one or more medical applications, including without limitation applications selected from the following list: the treatment of cancerous tumors, treatment of pathological target volumes, treatment of a pain, treatment of movement disorders, treatment of high blood pressure, treatment of cardiac malfunction, or treatment of tissue target volumes in nervous tissue, a nerve located within a bone, bone tissue, cardiac tissue, muscle tissue, or other types of bodily tissues.

Other examples of embodiments of systems and methods of the present invention are given in the rest of this patent. The details of embodiments of the invention are set forth in the accompanying drawings and description below. Other features, objects, and advantages of the invention will be apparent from the description and drawings and from the claims.

BRIEF DESCRIPTION OF THE DRAWINGS

In the drawings that constitute a part of the specification, embodiments exhibited various forms and features hereof are set forth, specifically:

FIG. 2A is a schematic diagram showing the assembly of coated medical cannula including a protrusion of the hub covered by the same coating that covers the cannula shaft.

FIG. 2B is a schematic diagram showing a medical probe including a removable stylet, an elongated shaft fixedly attached to a hub, a hub including a protrusion smaller than the main body of the hub, and a coating that covers a portion of the shaft and the protrusion of the hub.

FIG. 2C is a schematic diagram showing a coated probe including a shaft attached to a hub, the hub including a thin distal extension over the shaft, and tubing covering the said thin distal extension of the hub and some or all of the shaft which is not covered by the hub.

DETAILED DESCRIPTION OF THE INVENTION

Figure 1A:
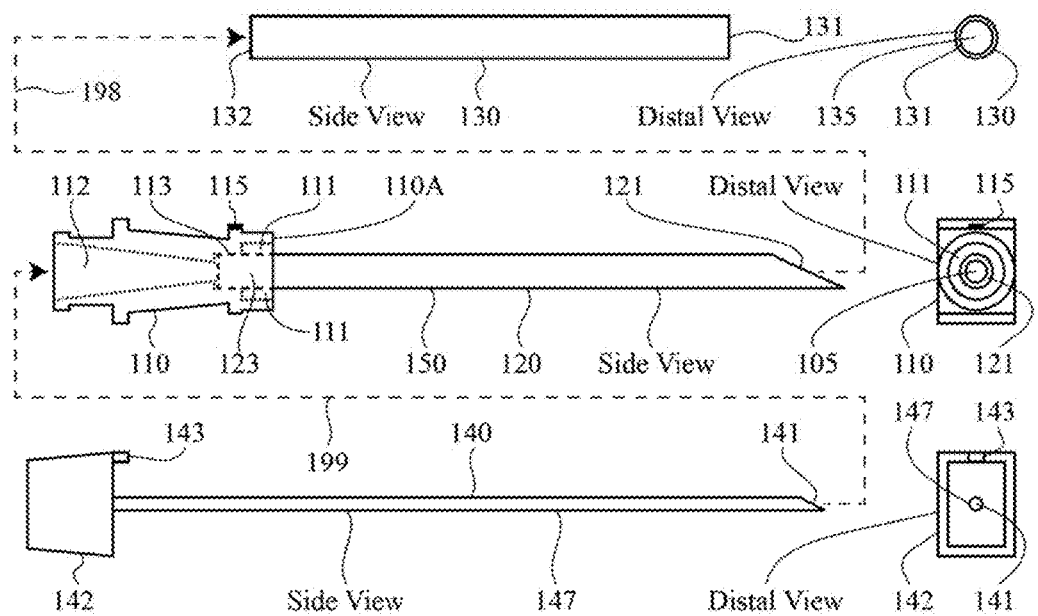
FIG. 1A is a schematic diagram showing the assembly of coated medical cannula including a recess in the cannula hub in which the coating of the cannula shaft is positioned.
Figure 1B:
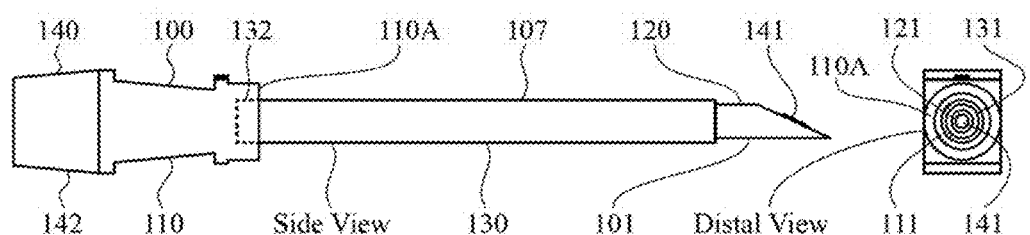
FIG. 1B is a schematic diagram showing a coated medical probe including a hub having a narrow recess in which a portion of the shaft coating is shrouded.
Figure 1C:
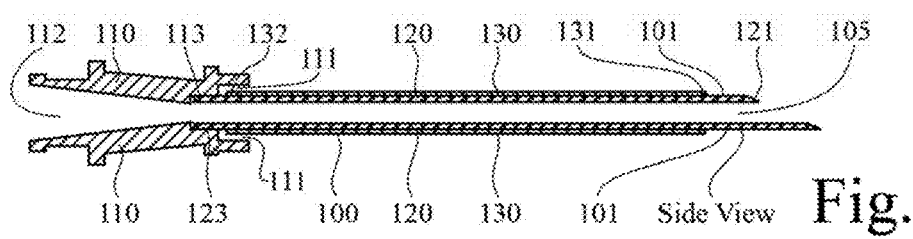
FIG. 1C is a schematic diagram showing probe including a shaft attached to a hub and partially covered by a coating, wherein the hub includes a distal slot in which the proximal end of the coating of the shaft is positioned.

Referring now to FIG. 1, in accordance with several aspects of the present invention, FIG. 1 refers collectively to FIG. 1A, FIG. 1B, and FIG. 1C. FIG. 1 presents schematically several embodiments of a coated medical probe. In one aspect, FIG. 1 relates to a medical probe including a hub, a shaft, and tubing covering all of, or at least a part of, the shaft. In several aspects, FIG. 1 relates to a radiofrequency electrode system configured for ablation of bodily tissue, and including a hub and an elongated shaft including at least a portion that is electrically insulative. In several aspects, FIG. 1 relates to the construction of a radiofrequency electrode. In several aspects, FIG. 1 relates to the construction of a radiofrequency cannula. In several aspects, FIG. 1 relates to the construction of a medical electrical probe being insulated across the junction between the probe hub and the probe shaft. In several aspects, FIG. 1 relates to medical electrode, such as an RF cannula or and RF electrode or a nerve-stimulation needle or a muscle-stimulation needle, including a hub into which electrical insulation covering the shaft of the medical electrode can slide.

FIG. 1 shows a medical probe 100 including a needle 150, electrical insulation 130 applied to the needle, and a removable stylet 140. In some embodiments of probe 100, the stylet 140 can be omitted. In some embodiments, the probe 100 can be a single-use RF cannula provided sterile to physicians and additionally including a recess 111 in the distal aspect 110A of the probe hub 110 in which the proximal end of the electrical insulation 132 of the cannula 100 is positioned. In some embodiments, probe 100 can be an RF cannula 100 including a cannula hub 110 into which electrical insulation 130 of the cannula shaft 120 can slide. In some embodiments, probe 100 can be an injectable stimulation needle including a hub 110 having a recess 111 in which the shaft electrical insulation 130 is shrouded. In some embodiments, the probe 100 can be an RF cannula including a shaft 120 attached to a hub 110, and an insulated shaft 107 having an active tip 101, wherein the hub 110 include a distal slot 111 in which the proximal end 132 of electrical insulation 130 covering the shaft 120 is positioned. In some embodiments, the probe 100 can be a recording electrode having continuous insulation over a portion of its shaft and manipulation hub. In some embodiments, probe 100 can be a single-use, sterile-packed RF cannula adapted for use with an RF electrode and including an elongated shaft 120 composed of stainless-steel hypotube; a plastic injection hub 110 modeled onto the shaft 120 and having a narrow cavity 111 around the elongated probe shaft 120 at the external, distal hub-to-shaft junction; thin heat-shrink insulation 130 partially shrouded within the cavity 111 of the hub 110, covering a proximal portion of the shaft 120; and leaving the remaining distal portion of the shaft 101 uninsulated. In some embodiments, probe 100 can be produced by means of the method of FIG. 3.

The hub 110 includes distal surface 110A, and a port 112 at the hub proximal end. The shaft 120 includes proximal end 123 and distal end 121. The insulative tubing 130 has proximal end 132 and distal end 131. The stylet includes a cap 142 at the proximal end of the stylet 140 and a bevel 141 at the distal end of the stylet 140. The assembled probe 100 includes a hub 110 at the probe proximal end and bevel point 121 at the probe distal end.

Figure 2D:
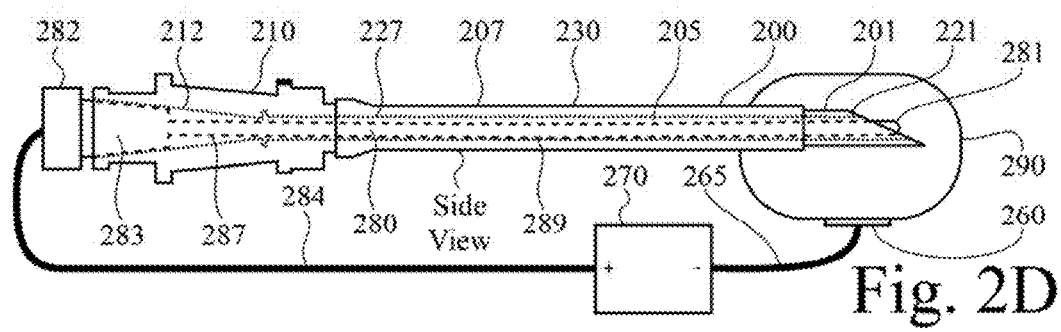
FIG. 2D is a schematic diagram showing an electrically-insulated needle whose shaft is attached to an electrically-insulating hub and includes both an electrically-insulated portion and an uninsulated tip region, wherein the electrical insulation covers a thin portion of the needle hub and a portion of the needle shaft, the uninsulated tip region is electrified by an electrical signal generator via an separate electrode positioned within the inner lumen of the needle shaft, and the needle shaft is positioned in bodily tissue on which a reference area electrode is positioned and configured to carry return current from the needle to the generator.

The needle 150 includes a hub 110 at the proximal end of the needle, and a cylindrical metallic shaft 120 at the distal end of the needle. The hub 110 is also at the proximal end of the assembled probe 100, and the shaft 120 is at the distal end of the assembled probe 100. The hub 110 and shaft 120 are inseparably connected, for example by glue, by an interference fit between the outer diameter of the shaft 120 and the inner diameter of a portion 113 of the hub 110, or by molding the hub 110 over the proximal end 123 of the shaft 120. The needle 150 includes a lumen 105 through its length that connects the hub port 112 to an opening in the distal bevel 121 of the needle shaft 120. The hub port 112 can be a luer port. The hub port 112 can be configured for injection of fluids. The hub port 112 can be configured to admit an electrode (such as an RF electrode) into the lumen of the metallic shaft 120 in order to electrify the metallic shaft 120 and the active tip 101 (as shown in FIG. 2D, for example). The inner lumen 105 can be sized to allow for admission of an electrode into the inner lumen and to ensure good electrical contact between the electrode outer surface and the inner surface of the metallic shaft 120. The inner lumen 105 can be sized to allow for injection of fluids into the port 112, through the inner lumen 105, out from the hole in the shaft point 121, and into bodily tissue in which the shaft 120 is positioned. The shaft can be hypodermic tubing, such as stainless steel hyptotube. The material of shaft 120 can include or be completely composed of stainless steel (such as 304-, 316-, 420-, or 440-type stainless steel) nitinol, titanium, silver, gold, platinum, and other surgical metals known to one skilled in the art of medical devices. The inner and outer diameters of shaft 120 can be sized for insertion into bodily tissue. The shaft 120 can have outer diameter in the range 0.1 mm to 5 mm. The shaft 120 can have outer diameter in the 34 gauge to 7 gauge, or larger. The shaft 120 can be composed of stainless steel hypotube having outer diameter in the range 23 gauge to 15 gauge, and having a wall thickness between the shaft inner and outer diameters that is selected from the range 0.002 inches to 0.015 inches, or larger, depending on physical limits defined by the outer diameter of the shaft, as is common for the shaft of an RF cannula. The shaft 120 can be tubing with thin wall, regular wall, heavy wall, and other wall thicknesses to define the inner diameter relative to the outer diameter of the shaft 120. The length of the shaft 120 can be a value selected from the list: 1 cm, 2 cm, 3 cm, 5 cm, 10 cm, 15 cm, 20 cm, 25 cm, 30 cm, a value greater than 30 cm, a value in the range 5 to 30 cm, and other lengths. The distal bevel 121 include a flat bevel with sharp edges configured for penetration of bodily tissue, such as the skin surface, blood vessels, muscles, liver tissue, kidney tissue, lung tissue, pancreatic tissue, spinal tissue, intraverebral disc material, bone, and other tissue types. The distal bevel 121 can have additional minor bevels to form a front or back tricut tip. The hub 110 can be sized to allow for manual manipulation of the needle 150, including movement of the needle 150 and torqueing of the needle 150 about its central elongated axis when the needle 150 is inserted into bodily tissue. The hub 110 can have maximum outer extent larger than outer diameter of the shaft 120. The hub 110 can have outer diameter in the range up to 1 cm or more. The hub 110 can have general geometry known to the art of medical needles, and additionally include a recess 111 in the hub distal end 110A. The hub 110 is constructed from an electrically-insulative material, such as a plastic like ABS, acrylic, delrin, ultem, polyethylene, polyuretrane, and other biocompatible material known to one skilled in the art of medical device engineering. In some embodiments, the hub 110 can include or be constructed from a metal, and can include a plastic coating or means of electrical insulation between the hub 110 and shaft 120 or between the hub 110 can any electrode inserted into port 112. The hub 110 includes an alignment indicator mark 115 that visually indicates the orientation of the shaft bevel 121 at the distal end of the shaft 120. In some embodiments, the marker 115 can visually indicate additional or other features that can be included in the shaft 120 or the tip 121, such a curve or bend in the shaft 120.

The recess 111 can be sized to provide narrow clearance between the outer surface of the shaft 120 and the inner surface of the recess 111. The recess 111 can be sized to provide narrow clearance between the outer surface of the tubing 130 within the recess and the inner surface of the recess 111. The recess 111 can be sized to provide sufficient clearance for the application of the end 132 of the tubing within the recess, and to provide narrow clearance between the outer surface of the tubing 130 within the recess and the inner surface of the recess 111. The recess 111 can be dimensioned to prevent tissue from substantially entering the recess 111 when the probe shaft 107 is completely inserted into bodily tissue such that the hub distal face 110A abuts the tissue surface. In some embodiments, the radial space from the outer surface of the shaft 120 and the outer surface of the insulation 130 to the inner surface of the recess 111 can be a value selected from the list: 0.0005 inches, 0.001 inches, 0.002 inches, 0.003 inches, 0.004 inches, 0.005 inches, 0.020 inches, a value between 0.005 and 0.020 inches, a value greater than 0.020 inches, a value less than 0.0005 inches. The depth of the recess 111 and the radial space from the outer surface of the shaft 120 and the outer surface of the tubing 130 to the inner surface of the recess can be configured to allow for application of the tubing 130 within the recess and prevention of tissue contacting an uncovered portion of the shaft 220 within the recess by consideration of the mechanical features and properties of the tissue surface, the depth of the recess 111, the length of the tubing 132 that is within the recess, and the spacing from the outer surfaces of the shaft 220 and tubing 130 to the inner surface of the recess 111. The depth of the recess can be a value selected from the list: 0.5 mm, 1 mm, 2 mm, 3 mm, a value less than 0.5 mm, a value greater than 3 mm, a value between 0.5 mm and 3 mm, a value configured to prevent tissue from contacting any uninsulated portion of the shaft 220 within the recess 111. In embodiments where the insulation is heat-shrink tubing, the depth of the recess 111 and the radial space from the outer surface of the shaft 120 and the outer surface of the tubing 130 to the inner surface of the recess 111 can be configured to accommodate the expanded outer diameter (OD) of the tubing 130, the degree of longitudinal shrinkage due to heating of the tubing 130, and the wall thickness of the tubing 130, in order to allow the tubing 130 to enter the recess when the tubing is in an expanded state, and to ensure tissue does not touch any uninsulated portion of the shaft 220 within the recess 111 after the tubing 130 has been recovered by heating.

The electrical insulation 130 is a tubular structure that is electrically insulative at electrical signal frequencies intended to be delivered deliver to bodily tissue via the probe 100. Said signal frequencies can include radiofrequency signal frequencies, microwave (MW) signal frequencies, the signal frequencies associated with nerve stimulation signals, the signal frequencies associated with muscle stimulation signals, high frequency signal frequencies, low frequency signal frequencies and other signal frequencies applied via probes and other electrodes to bodily tissue. The insulation 130 can have a high dielectric constant. The dielectric breakdown (also known as the dielectric strength) of the insulation 130 can be greater than 500 V/m. The electrical insulation 130 can have a wall thickness selected from the list: a value in the the range 0.00025 to 0.005 inches, a value less than 0.00025 inches, a value greater than 0.005 inches. The electrical insulation can have wall thickness in the range 0.001 to 0.002 inches. The electrical insulation 130 can have wall thickness configured to suit clinical needs, mechanical constraints, and/or electrical requirements. The insulation 130 can be composed of a material known the art of medical device design, such as PTFE, FEP, PET, polyolefin, polyurethane, polyimide, nylon, and other materials for medical tubing. The insulation 130 can be heat-shrinkable tubing, such as PTFE, FEP, PET, polyolefin, and other materials known in the art of medical device coating, such as needle, wire, guidewire, and coil coating. The insulation 130 can be tapered and/or adhered to the shaft 220 at the distal insulation end 131. The electrical insulation 130 can have an inner dimension configured to slide over the outer surface of the shaft 120 and into the hub recess 111. The tubing 130 can be fixed to the needle 150 by gluing or bonding the tubing 130 to the shaft 120. The tubing 130 can be fixed to the needle 150 by heat shrinking the tubing 130 over the needle shaft 120. When the insulation 130 is applied to the needle shaft 120, the proximal end 132 of the insulation 130 is positioned in the recess 111 in the distal end 110A of the hub 110.

The stylet 140 comprises an enlongated shaft 147 sized to enter the inner lumen 105 of needle 150, and cap 142 configured to enlarge with hub 110 to set the relative position of the stylet shaft 147 and the needle shaft 120, including the relative positions of the stylet distal end 141 and the needle distal end 121. The cap 142 includes a tab 143 that engages with a slot in the needle hub to rotationally align the stylet flat bevel 141 to the needle flat bevel 121, to form a substantially solid, flat bevel tip when the stylet 140 is fully inserted into the needle 150.

In some embodiments, the shaft 120 can be a solid rod without and inner lumen. In some embodiments, the shaft 120 can have a bent tip, such as a shaft having a bend approximately 10 mm from the distal end of the shaft to provide for steerability in bodily tissue. In some embodiments, the shaft point have a geometry selected from the list: closed distal end, blunt tip, blunt tip with side port, sharp tip with side port configured to provide for the sideward exit of an electrode inserted into the inner lumen 105 of the shaft 120, blunt tip with side port configured to provide for the sideward exit of an electrode inserted into the inner lumen 105 of the shaft 120, solid trocar tip, solid trocar tip with injection-outflow side port, tuohy, crawford, hustead, weiss, sprotte spezial, epidural-type tip, tip configured for passage of a catheter, tip configured for introduction of an epidural catheter, square tip, square tip with tapered sharpened distal edge, non-coring tip, spinal needle tip, quincke, sise tip, kirschner, lemmon, whitacre, crawford tip, lutz, hanaoka, sprotte, courand, seldinger, franseen, chiba, tip matched to the stylet tip 141 geometry, and other medical needle tip geometries. In these embodiments, the stylet 141 can have one of a variety of geometries matched to the shaft bevel 121 in order to serve a functional need, such as forming a substantially solid distal needle point that facilitate penetration of bodily tissue with minimal coring. In some examples, the shaft tip 121 and stylet bevel 141 can be configured to provide for penetration into bone, such as vertebral bone or any bone in the body, for access to nerve within bone, osteoid osteoma, bone tumors, or another intra-bone structures. In some embodiments, the stylet shaft 147 can have a length sized to extend beyond the distal end 121 of the needle shaft 120. In some embodiments, the probe 100 can be configured to be placed in a specific part of the body such as the spine, a blood vessel, the epidural space, the spinal cord, a visceral organ, the liver, the kidney, the pancreas, the lung, the brain, a gland, the tyroid, the adrenal gland, a bone, a vertebral bone. In some embodiments, the electrical insulation 130 can be an electrically-insulative coating, such as a coating that can be painted or sprayed onto the needle shaft 120, such as an elastomeric coating, powered paint, fluid paint, or another kind of paint. In some embodiments, the probe 100 can additionally include an integral connection to an electrical generator, such as an RF generator (by analogy, in one example, to the adaptation of probe 200 in FIG. 2H). In some embodiments, the probe 100 can additionally include an integral connection to an electrical generator, such as an RF generator (by analogy, in one example, to the adaptation of probe 200 in FIG. 2H) and can include a connection to a fluid pump that circulates fluid within and/or through the probe shaft 107 (thereby forming an internally-cooled and/or perfusion unitized electrode). In some embodiments, the probe 100 can additionally include an integral fluid injection tube (by analogy, in one example, to the adaptation of probe 200 in FIG. 2H). In some embodiments, the probe 100 can additionally include an integral fluid injection tube and an integral connection to an electrical signal generator, such as an RF generator, MW generator, nerve-stimulation generator, and/or muscle stimulation generator (by analogy, in one example, to the adaptation of probe 200 in FIG. 2H). In some embodiments 100 tubing 130 can be electrically-insulative and the probe 100 can be adapted for use with an separate non-cooled, internally-cooled, or perfusion ablation electrode, such as an RF electrode (by analogy, in one example, to the configuration of probe 200 in FIG. 2D). In some embodiments, an electrode fully inserted in the lumen 105 of probe 100 can protrude substantially from the end 121 of the probe 100 (for example by up to 60 mm, or more) to form a combined active tip with the probe active tip 101. In some embodiments, the shaft 107 can be fully insulated and an electrode inserted into lumen 105 can protrude from the bevel 121 to form the active tip of the combination of the probe 100 and the electrode.

Referring now to FIG. 1A, the assembly of the probe 100 is shown in a schematic diagram. Each of the insulation 130, the needle 150, and the stylet 140 is shown in two perpendicular external views, labeled "Side View" and "Distal View", wherein the "Side View" shows a view from the side of the proximal-distal axis of element, and the "Distal View" shows a view of the distal end of the element, perpendicular to the proximal-distal axis. The injection port 112, recess 111, and the inner surfaces of the hub 110 are shown by dotted lines through the walls of the hub 110. The proximal end 123 of the shaft 120 is shown as a dashed line through the walls of the hub. The hub 110 is connected fixedly to the shaft 120 at interface 113. As shown by dotted arrow 198, the needle 150 is inserted into the inner lumen 135 of the insulation 130 and fixed to the electrical insulation 130, for example by heat shrinking or gluing, and the insulation proximal end 132 is positioned within the hub recess 111.

In configurations for which insulation 130 is heat shrink tubing, the expanded outer diameter of the tubing 130 and the inner diameter of the hub recess 111 are sized so that the expanded tubing 130 (ie not yet shrunk by the application of heat) can slide within the recess 111. The expanded inner diameter of the heat-shrink tubing 130 and the outer diameter of the shaft 120 are sized so that the expanded insulation 130 can slide over the shaft 120. The recovered inner diameter of the heat-shrink tubing 130 (ie after heat has been application of shrinking heat) and the outer diameter of the shaft 120 are sized so that the recovered tubing 130 tightly and smoothly shrinks over the outer diameter of the shaft 120. Heat shrink tubing 130 tends to contract both longitudinally (ie in the proximal-distal direction) and radially when sufficient heat is applied to induced recovery (ie shrinking) of the tubing 130; as such, the longitudinal dimension of the recess 111 (ie the depth of the recess 111) is sized such that when unrecovered tubing 130 is fully inserted into the recess and shrinking heat is applied, the proximal end 132 of the heat-shrink tubing 130 will consistently remain within the hub recess 111 at a depth that prevents tissue from contacting any uncovered portion of the shaft 120 within the recess 111. The shrinking properties of the heat-shrink tubing 130, the orientation of the needle 150 relative to gravity, and other fixturing can also be engineered to help ensure its proximal end 132 remains in the recess 111 after recovery.

The stylet 140 is inserted into the probe hub port 112 and probe inner lumen 105 as shown by dotted arrow 199. The stylet 140 is configured to be removable and replaceable by the end-user in the course of performing a medical procedure.

Referring now to FIG. 1B, the assembled probe 100 is shown in a schematic diagram with the stylet 140 fully inserted into the probe inner lumen 105 via port 112 such that the stylet cap 142 abuts the plastic probe hub 110. The probe 100 is shown in two perpendicular external views labeled "Side View" and "Distal View", wherein the "Side View" shows a view from the side of the proximal-distal axis of probe 100, and the "Distal View" shows a view of the distal end of the probe 100, perpendicular to the proximal-distal axis of the probe 100. The proximal end 132 of the insulation is shown as a dotted line and is recessed in the recess 111 of the hub 110. The shaft 107 of the probe 100 includes the insulated portion of the needle shaft 120 that is distal to the hub 110, and the uninsulated portion 101 of the shaft 120 that is distal to the insulation 130 covering the shaft 220. The length of shaft 107 can be a length selected from the range 10 mm to 300 mm or longer, depending on the medical application. Lengths less than 10 mm for shaft 107 can also be used for some applications. Typical shaft lengths for percutaneous nerve ablation in the spine are 50, 60, 100, 120, 150, 200 mm. Typical shaft length for percutaneous tumor ablation in large organs are 100, 150, 200, 250 mm or longer. The uninsulated portion 101 of the probe shaft 107 is the active tip of the probe 100. By means of an adaptation of probe 100 analogous the adaptations of probe 200 in FIGS. 2D and 2H, electrical energy, such as RF energy, can be delivered from the active tip 101 to bodily tissue in which the probe shaft 107 is positioned, whereas electrical energy does not flow from the insulated portion of the probe shaft 107 into bodily tissue in which the probe shaft 107 is in contact. The length of the active tip can be a value selected from the range 0.25 mm to 60 mm or more, depending on the medical application. In some embodiments, almost the entirety of the shaft 107 is uninsulated. Typical active tip lengths for nerve ablation are 2, 4, 5, 6, 10, 15, 20 mm. Typical active tip lengths for tumor ablation in large organs are 10, 20, 25, 30, 35, 40, 50, 60 mm. Typical active tip lengths for tissue coagulation are 10, 20, 25, 30, 35, 40, 50, 60, 100 mm or longer. Typical active tip lengths for stimulation-guided nerve blocks are 1mm or less. The stylet distal flat bevel 141 is aligned longitudinally and rotationally with the probe bevel 121 by the interlocking of the stylet cap 142 and the hub 110. One advantage of the probe 100 is that the proximal end of the insulation 130 applied to the shaft 120 is shrouded in the recess 111 at the distal end of the hub 110, and as such, the full length of the probe shaft 107 can be inserted into bodily tissue such that the bodily tissue abuts the distal end 110A of the hub 100 without any uninsulated metal portion of the shaft 107 contacting the bodily tissue, except for the active tip 101; as such, electrical energy (such as radiofrequency energy) applied to the probe 100 by insertion of an electrode into the probe inner lumen 105 (in analogy to the configuration of probe 200 shown in FIG. 2D) is prevented from being applied to said bodily tissue through the plastic hub 110 and along the entire probe shaft 107 except for the active tip 101. The clearance between the inner surface of the recess 111 and the outer surface of the insulation 130 and the shaft 120 can be configured to be small relative to the curvature of the expected surface of bodily tissue (such as the skin surface, or the surface of an organ) into which the probe is designed to be inserted to prevent tissue from entering the recess 111 and contacting any insulated metal portion of the shaft 120 inside the recess 111.

Referring now to FIG. 1C, the assembled probe 100 is shown in a schematic diagram with the stylet 140 removed. The probe 100 is shown in a cross-sectional view through the centerline of the probe 100, showing the proximal-distal, longitudinal axis of probe 100. The fixed attachment between the metal shaft 120 and inner surface 113 of the plastic hub 110 is shown. The positioning of the insulation proximal end 132 within the hub recess 111 is shown. The insulation 130 covers the shaft 120. The distal end 131 of the insulation 130 stops near the end of the shaft 120 to leave a portion of the shaft 101 insulated. This portion 101 is the active tip. Electrical signals from an electrode contacting the shaft 120 (for example, in the manner shown in FIG. 2D for probe 200) will conduct along the metal shaft 120 to the active tip 101 from which the said signals can be applied to tissue. A stylet 140 or electrode inserted into port 112 will smoothly enter in the lumen of the shaft 120, and will exit the hole in the distal bevel 121 if the stylet 140 or electrode is long enough. Fluid injected into port 112 will flow through the lumen 105 and out from the hole in the distal end 121 of the shaft 107.

Referring now to FIG. 2, in accordance with several aspects of the present invention, FIG. 2 refers collectively to FIG. 2A, FIG. 2B, FIG. 2C, FIG. 2D, FIG. 2E, FIG. 2F, FIG. 2G and FIG. 2H. FIG. 2 presents schematically several embodiments of a coated medical probe. In several aspects, FIG. 2 relates to a medical probe including a hub and including tubing covering all of, or at least a part of, the probe shaft. In several aspects, FIG. 2 relates to a radiofrequency electrode system configured for ablation of bodily tissue, and including a hub and an elongated shaft including at least a portion that is electrically insulative. In several aspects, FIG. 2 relates to the construction of a radiofrequency electrode. In several aspects, FIG. 2 relates to the construction of a radiofrequency cannula. In several aspects, FIG. 2 relates to the construction of a medical electrical probe being continuously insulated across the junction between the probe hub and the probe shaft. In several aspects, FIG. 2 relates to medical electrode, such as an RF cannula or and RF electrode or a nerve-stimulation needle, including a hub over which the electrical insulation covering the shaft of the medical electrode can slide.

FIG. 2 shows a medical probe 200 including a needle 250, electrical insulation 230 applied to the needle, and a removable stylet 240. In some embodiments of probe 200, the stylet 240 can be omitted. In some embodiments, the probe 200 can be a single-use RF cannula provided sterile to physicians and additionally including a protrusion 211 from the distal aspect 210A of the probe hub 210 over which the proximal end of the electrical insulation 232 of the cannula 200 is positioned. In some embodiments, probe 200 can be an RF cannula including a cannula hub 210 over which electrical insulation 230 of the cannula shaft 220 can slide. In some embodiments, probe 200 can be an injectable stimulation needle including a hub 210 having a distal extension 211 which the shaft electrical insulation 230 covers. In some embodiments, the probe 200 can be an RF cannula including a shaft 220 attached to a hub 210, and an insulated shaft 207 having an active tip 201, wherein the hub 210 includes a thin distal taper 211 over which the proximal end 232 of electrical insulation 230 covering the shaft 220 is positioned. In some embodiments, the probe 200 can be a recording electrode having continuous insulation over a portion of its shaft and manipulation hub. In some embodiments, probe 200 can be a single-use, sterile-packed RF cannula adapted for use with an RF electrode and including an elongated shaft 220 composed of stainless-steel hypotube, a plastic injection hub 210 modeled onto the shaft 220 and having a thin protrusion 211 over the elongated probe shaft 220, thin heat-shrink insulation 230 covering a part of the thin protrusion 211 of the hub 210 and a proximal portion of the shaft 220, the thin heat-shrink insulation 230 leaving the remaining distal portion of the shaft 201 uninsulated. In some embodiments, probe 200 can be produced by means of the method of FIG. 4.

The hub 210 includes distal surface 210A and a port 212 at the hub proximal end. The needle shaft 220 includes proximal end 223 and distal end 221. The insulative tubing 230 has proximal end 232 and distal end 231. The stylet includes a cap 242 at the proximal end of the stylet 240, and a bevel 241 at the distal end of the stylet 240. The assembled probe 200 includes a hub 210 at the probe proximal end and bevel point 221 at the probe distal end.

The probe 200 and its constituents parts (namely the needle 250, the insulation 230, and the stylet 240) can the same dimensions, materials, performance characteristics, and/or intended uses as the probe 100 and its constituent parts (namely the needle 150, the insulation 130, and the stylet 140, respectively). The probe 200 can have similar variations of geometry and parts in various embodiments, as detailed for probe 100. The main body of hub 210 of probe 200 is sized for manual manipulation of the probe 200 within bodily tissue, including rotation and translation. The distal prominence 211 of the hub is has a small external diameter to allow the same electrical insulation 230 that is tight to the shaft 220 to overlap the hub prominence 211. The protrusion 211 of the hub 210 extends over the shaft 220 and completely surrounds the shaft external circumference of the shaft over the length of the protrusion 211. In some embodiments, the protrusion 211 can have additional length over which the protrusion 211 does not completely surround the shaft 220.

Referring now to FIG. 2A, the assembly of the probe 200 is shown in a schematic diagram. Each of the insulation 230, the needle 250, and the stylet 240 is shown in two perpendicular external views, labeled "Side View" and "Distal View", wherein the "Side View" shows a view from the side of the proximal-distal axis of element, and the "Distal View" shows a view of the distal end of the element, perpendicular to the proximal-distal axis of the element. The injection port 212 and the inner surfaces of the hub 210 are shown by dotted lines through the walls of the hub 210. The proximal end 223 of the shaft 220 inserted into the hub 210 is shown as a dashed line through the walls of the hub 210. The hub 210 is connected fixedly to the shaft 220 at interface 213, for example by glue, insert-molding, or a tight interference fit. As shown by dotted arrow 298, the needle 250 is inserted into the inner lumen 235 of the insulation 230 and fixed to the electrical insulation 230, for example by heat shrinking or gluing, and the insulation proximal end 232 is positioned over the hub protrusion 211. The wall thickness of the hub prominence 211 outside the shaft 220 can be in the range 0.0005 inches to 0.005 inches or more, depending on the type of insulation 230. When the hub 110 is insert-molded onto the shaft 220 it is advantageous that the prominence 211 is thick enough to ensure a consistent wall thickness of prominence 211 and to avoid holes in the prominence 211 that can arise if the shaft 220 and the hub 110 are not perfectly concentric. The length of the prominence 211 distal to the distal hub surface 210A can be a value selected from the list: a values less than 0.5 mm, 0.5 mm, 1 mm, 2 mm, 3 mm, a value greater than 3 mm, a value between 0.5 mm and 3 mm. The length of the prominence 211 can be configured to ensured that coating 230 can be consistently positioned and fixed to the shaft 220 and prominence 211 such that there is no uninsulated portion of the shaft 220 at the junction between the prominence 211 of the hub 210 and the shaft 220. The main body of the hub 210 that is proximal to the distal face 210A is sized for manual manipulation and fluid injection, and the main body of the hub is larger than the prominence which is size to interface with the shaft insulation; as such the prominence is thin relative to the maximum outer extent of the hub 210. In other embodiments of probe 200 where the hub is smaller, the prominence can be of similar size or even smaller than the prominence to suit ergonomic, weight, electrical, and other functional constraints.

In configurations for which insulation 230 is heat shrink tubing, the expanded inner diameter of the tubing 230 and the outer diameter of the hub taper 211 are sized so that the expanded tubing 230 (ie not yet shrunk by the application of heat) can slide over the hub protrusion 211. The expanded inner diameter of the heat-shrink tubing 230 and the outer diameter of the shaft 220 are sized so that the expanded insulation 230 can slide over the shaft 220. The recovered inner diameter of the heat-shrink tubing 230 (ie after heat has been application of shrinking heat), the outer diameter of the protrusion 211, and the outer diameter of the shaft 220 are sized so that the recovered tubing 230 tightly and smoothly shrinks over both the outer surface of the protrusion 211 and the outer diameter of the shaft 220. Heat shrink tubing 230 tends to contract both longitudinally (ie in the proximal-distal direction) and radially when sufficient heat is applied to induced recovery (ie shrinking) of the tubing 230; as such, the longitudinal dimension of the protrusion 211 (ie the length of the protrusion 211) is sized such that when unrecovered tubing 230 fully covers the protrusion 211 and shrinking heat is applied to the tubing 230, the proximal end 232 of the heat-shrink tubing 230 will consistently remain covering a portion of the hub protrusion 211. The shrinking properties of the heat-shrink tubing 230, orientation of the needle 250 relative to gravity during shrinking, the size and geometry of the prominence 211, and other fixturing can also be selected to help ensure its proximal end 232 remains over the prominence 211 after recovery. Features on the outer surface of the protrusion 211 (such as bumps, ridges, depressions, grooves, surface roughing, and combinations thereof) can be included to ensure overlap and a mechanical lock between insulation 230 and protrusion 211; some examples of such features are shown on protrusion 211F of FIG. 2F. In some embodiments, it can be advantageous that the distal hub protrusion 211 has maximum outer width in the range 0.004 to 0.006 inches larger than the outer diameter of the needle shaft 220, for example to ensure concentricity in the application of the shaft 220 to the hub 210 and thus consistencies of the wall thickness of the prominence 211, and to allow for heat-shrink tubing both to slide over the prominence 211 and to shrink tightly to the shaft 220.

Referring to FIG. 2A, protrusion 211 includes cylindrical proximal section and a distal taper 211A. The taper 211A has the advantage of facilitating the sliding of insulation 230 over the protrusion 211. The taper 211A has the advantage progressively increasing the degree of mechanical interference and interlock between the insulation tube 230 and the hub prominence 211 as the insulation 230 is slid over the prominence 211 during assembly of the probe 200.

The stylet 240 is inserted into the probe hub port 212 and probe inner lumen 205 as shown by dotted arrow 299. The stylet 240 is configured to be removable and replaceable by the end-user in the course of performing a medical procedure.

Referring now to FIG. 2B, the assembled probe 200 is shown in a schematic diagram with the stylet 240 fully inserted into the probe inner lumen 205 such that the stylet cap 242 abuts the plastic probe hub 210. The probe 200 is shown in two perpendicular external views labeled "Side View" and "Distal View", wherein the "Side View" shows a view from the side of the proximal-distal axis of probe 200, and the "Distal View" shows a view of the distal end of the probe 200, perpendicular to the proximal-distal axis of the probe 200. The outer surface of the distal end of the hub protrusion 211 is shown as a dotted line through the wall of the proximal portion 232 of the insulation 230. A portion of the outer surface of the shaft 220 is shown as a dashed line through the wall of the insulation 230. The shaft 207 of the probe 200 includes the insulated portion of the needle shaft 220 that is distal to the hub 210, and the uninsulated portion 201 of the shaft 220 that is distal to the insulation 230 covering the shaft. The uninsulated portion 201 of the probe shaft 207 is the active tip of the probe 200. Electrical energy, such as RF energy, can be delivered from the active tip 201 to bodily tissue in which the probe shaft 207 is positioned, whereas electrical energy does not flow from the insulated portion of the probe shaft 207 into bodily tissue in which the probe shaft 207 is in contact. The stylet distal flat bevel 241 is aligned longitudinally and rotationally with the probe bevel 221 by the interlocking of the stylet cap 242 and the hub 210 by means of cap tab 243. One advantage of the probe 200 is that the proximal end of the insulation 230 applied to the shaft 220 overlaps the distal part of the hub 211, and as such, the full length of the probe shaft 207 can be inserted into bodily tissue 290 such that the bodily tissue abuts the distal end 210A of the hub 200 without any uninsulated metal portion of the needle shaft 220 contacting the bodily tissue, except for the active tip 201; as such, electrical energy (such as radiofrequency energy) applied to the probe 200 by insertion of an electrode into the probe inner lumen 205 (as shown in one example by the configuration of FIG. 2D) is prevented from being applied to said bodily tissue through the plastic hub 210 and along the entire probe shaft 207 except for the active tip 201.

Referring now to FIG. 2C, the assembled probe 200 is shown in a schematic diagram with the stylet 240 removed. The probe 200 is shown in a cross-sectional view through the centerline of the probe 200, showing the proximal-distal, longitudinal axis of probe 200. The fixed attachment between the metal shaft 220 and inner surface 213 of the plastic hub 210 is shown. The positioning of the insulation proximal end 232 over the hub extension 211 is shown. The insulation 230 covers the shaft 220. The distal end 231 of the insulation 230 stops near the end of the shaft 220 to leave a portion of the shaft 201 insulated. This portion 201 is the active tip. Electrical signals from an electrode contacting the shaft 220 (for example, in the manner shown in FIG. 2D or in the manner shown in FIG. 2H) will conduct along the metal shaft 220 to the active tip 201 from which the said signals can be applied to tissue. A stylet 240 or electrode inserted into port 212 will smoothly enter in the lumen of the shaft 220, and will exit the hole in the distal bevel 221 if the stylet 240 or electrode is long enough. Fluid injected into port 212 will flow through the lumen 205 and out from the hole in the distal end 221 of the shaft 207.

Referring now to FIG. 2D, the assembled probe 200 is shown in a schematic diagram that presents one embodiment of the operation of probe 200 with a separate electrode 280. The probe is inserted into bodily tissue 290 and the stylet 240 is replaced by an electrode 280 fully inserted into the probe inner lumen 205 such that the distal electrode hub 283 interlocks with the hub port 212. The inner surface of the probe 200 which surround the lumen 205 are shown within the probe 200 as dotted lines and include the inner surface of the port 212 and the inner surface of the shaft 227. The probe 200 is shown in an external view from the side showing the proximal-distal axis of the probe 200. The electrode 280 includes elongated conductive metal shaft 287, proximal hub 282 including a distal taper 283 configured to interface with probe port 212, and distal shaft point 281 that includes a temperature sensor (such as a thermocouple or thermistor) and that is aligned with the probe bevel 221. In some embodiments, the temperature sensor 281 can be omitted. The distal electrode hub 283 and proximal electrode shaft is shown as a dotted line through the wall of probe 200. The electrode conductive shaft 287 touches the inner surface of the conductive needle shaft 220 at point 289 so that an electrical signal applied to the electrode shaft 287 is conducted to the needle shaft 220 and the probe active tip 201. In some embodiments, there can be more than one point of contact. The inner diameter of the needle shaft 220, the outer diameter of the electrode shaft 287, the curvature of the electrode shaft 287, and the position of the electrode shaft 287 relative to the central axis of the lumen 205 can each be sized and configured to ensure consistent electrical contact between the electrode shaft 287 and the inner surface of the shaft 220. The electrode 280 is attached to one pole (labeled "+") of the electrical signal generator 270 via cable 284, which conducts electrical current from the +pole of the generator 270 to the metallic electrode shaft 287. Cable 284 also carries temperature information from the temperature sensor in the distal tip 281 of the electrode 280 to the generator 270, which can display the temperature information to the user and control the generator signal output using the temperature information. Cable 284 can take a variety of forms, including one selected from the list: integral to the electrode 280 and plugged into a connector of the generator 270, integral to the generator 270 and plugged into a connector of the electrode 280, plugged into a connector on the generator 270 and a connector on the electrode 280, composed of two parts of which the first part is integral to the electrode 280 and the second part is plugged into the generator 270 and the first part, and other forms of electrode cable known in the art of medical electrodes. The other pole of the generator 270 is labeled "−" and is connected to reference electrode 260 via cable 265. Reference electrode 260 is a plate-style electrode, such as an electrosurgical ground pad, configured to carry return current from a probe type electrode and to distribute said return current over an area of the surface of bodily tissue 290 to prevent high current densities at the locations of return current. In some embodiments, the generator 270 can include an RF signal generator. In some embodiments, the generator 270 can include a nerve-stimulation signal generator. In some embodiments, the generator 270 can include a microwave signal generator. In some embodiments, the generator 270 can include a PENS signal generator. The distal end of the probe 200 is inserted into bodily tissue such that the active tip 201 is within the bodily tissue 290. When the generator 270 applies a voltage signal across its two poles +and −, current flows from the active tip 201 of the probe 200 and the portion of the electrode tip 281 protruding from the probe bevel 221, through the bodily tissue 290, and to the reference pad 260. In the case of an alternative voltage signal, such as a radiofrequency signal or biphasic stimulation pulse, current flows in both directions between the active tip 201 and the pad 260. In the case of radiofrequency ablation, high current densities near the active 201 can directly affect nerves and heat the tissue, and a temperature sensor in the electrode tip 281 can be used for the generator 270 to control the tissue temperature by varying characteristics of the radiofrequency signal.

In some embodiments, the generator 270 can be connected to multiple electrodes and probes and/or multiple ground pads at the same time. In some embodiments, the generator 270 can include more than two output poles. In some embodiments, the electrode 280 can be an internally-cooled electrode having a connection to a fluid pump that circulates water, saline, cryogenic coolant, or another coolant agent through the electrode shaft 287. In some embodiments, the electrode shaft 287 protrudes substantially distally to the distal end of the probe 200 and produces an elongated active tip with the probe tip 201. In some embodiments, the probe shaft 207 is fully insulated, and the electrode protrudes from the distal end of the probe 200 and itself solely form the active tip of the assembly of the electrode 280 and the probe 200. In some embodiments, insulation 230 can be a spray-on or paint-on insulation (such as a plastic paint, power coating, or elastomeric coating) that overlaps both the shaft 220 and the hub 210 of needle 250. In some embodiments, the insulation can be plastic tubing that can slide over both the needle shaft 220 and the hub prominence 211 and be fixed to both by means of glue between the inner surface of the tubing 230 and the outer surface of the shaft 220 and/or the hub prominence 211. In some embodiments, the active tip 201 can be positioned at an intermediate position along the shaft 207, and an additional segment of insulation can be applied to the shaft 220 distal that that active tip 201. In some embodiments, the active tip 201 can be a slot in one side of the electrical insulation 230 configured to apply electrical energy asymmetrically about the probe shaft 200. In some embodiments, the probe 200 in FIG. 2D is configured for tissue ablation, such as RF tissue ablation, within tissue 290.

Figure 2E:
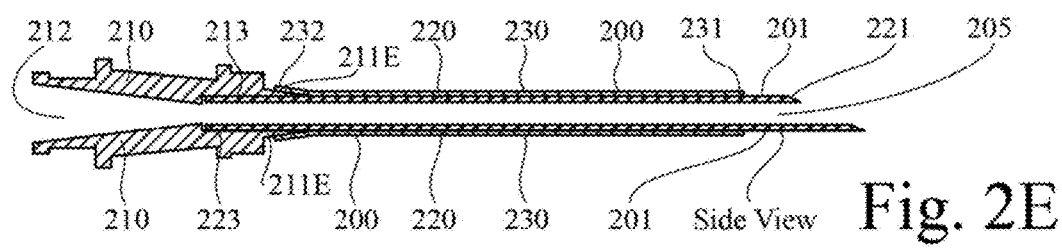
FIG. 2E is a schematic diagram showing a medical probe having a hub and a shaft over both of which a coating is positioned, wherein the hub tapers to the shaft smoothly.

Referring now to FIG. 2E, the assembled probe 200 is shown in a schematic cross-sectional view and has a distal hub protrusion 211E having an alternative fully-tapered geometry. Protrusion 211E has a continuous taper from the hub distal face 210A to the outer surface of the needle shaft 220. One advantage of the continuous taper 211E is that application of tubular insulation 230 having tight clearance to the prominence 211 can be easier and smoother than if prominence 211 has a flat portion.

Figure 2F:
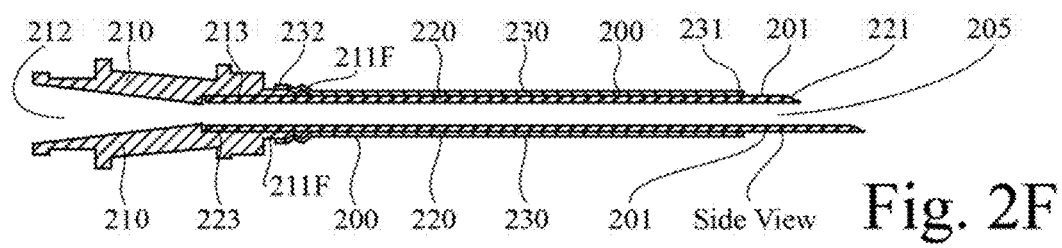
FIG. 2F is a schematic diagram showing a probe having a hub and a shaft over both of which a coating is positioned, wherein the hub includes a thin portion that extends over the shaft, the said portion having an irregular external surface configured to mechanically interlock with the coating covering it.

Referring now to FIG. 2F, the assembled probe 200 is shown in a schematic cross-sectional view and has a distal hub protrusion 211F having an alternative textured geometry. Protrusion 211F has both peaks and depressions that provide for mechanical interlocking with the insulation 230. One advantage of a textured taper 211F is that the tubular insulation 230 is less likely to shift during application. One advantage of a textured taper is that the tubular heat-shrink insulation 230 is less likely to slide along the shaft 220 and protrusion 211F as the insulation 230 is shrunk down onto the hub prominence 211F and the shaft 220. One advantage of a textured taper is that the tubular heat-shrink insulation 230 is less likely to slide along the shaft 220 in use. In some embodiments, the hub prominence 211F has only one peak in its outer surface. In some embodiments, the prominence 211F has only one depression in its outer surface. In some embodiments, a peak can be a bump or ridge. In some embodiments, a depression can be a pit or a groove. In some embodiments, the outer surface of the prominence 211F is textured by sand blasting or bead blasting.

Figure 2G:
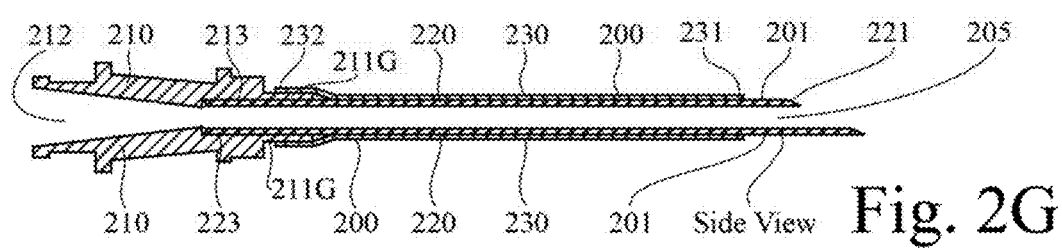
FIG. 2G is a schematic diagram showing a medical probe having a hub and a shaft over both of which a coating is positioned, wherein the hub includes a thin cylindrical portion which extends over the shaft and over which the coating is positioned.

Referring now to FIG. 2G, the assembled probe 200 is shown in a schematic cross-sectional view and has a distal hub protrusion 211G having an alternative square-end, cylindrical geometry. Protrusion 211G has a substantially constant diameter over its entire length. The insulation 230 smoothes over the transition from the distal face of the prominence 211G and the outer diameter of the shaft 220. One advantage of the cylindrical prominence 211G is that the degree of electrical insulation is constant over the length of the hub prominence 211G.

Figure 2H:
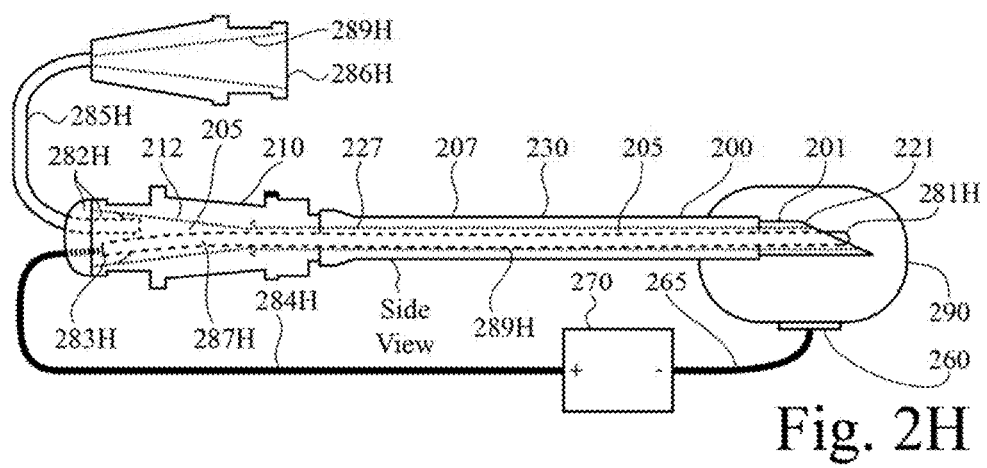
FIG. 2H is a schematic diagram showing a unitized, tissue-piecing, injection electrode whose shaft is attached to an electrically-insulating hub and includes both an electrically-insulated portion and an uninsulated tip region, wherein the electrical insulation covers a thin portion of the electrode hub and a portion of the electrode shaft, the uninsulated tip region is electrified by an electrical signal generator via a connection integral to the electrode, the electrode includes an integral flexible fluid injection-port tube configured to provide for simultaneous injection of fluid through the electrode shaft and connection to the electrical signal generator, and the electrode shaft is positioned in bodily tissue on which a reference area electrode is positioned and configured to carry return current from the needle to the generator.

Referring now to FIG. 2H, the probe 200 is shown in a schematic external side view, and is adapted to be a unitized, tissue-piecing, injection electrode. Probe 200 is integrally connected to fluid injection port 286H via a flexible tube 285H, which can, in one embodiment, be a plastic tube such as a polyurethane tube or another type of tube known in the art of medical device engineering. The port 286H includes a luer taper 289H which is shown as a dotted line through the side wall of the port 286H. The tubing 285H penetrates a closure 282H at the proximal end of the hub 201 and enters the lumen 205 within the hub 210. The tubing 285H is shown as a dotted line within the hub closure 282H and the hub 210. In some embodiments, the closure 282H can be glue, a cap, an external hub wall, or a combination thereof. Part of the closure 282H is shown as a dotted line within the hub 210. The closure 282H physically captures the tubing 285H and creates a fluid seal with the tube 285H to prevent substantially fluid outflow from the lumen 205. Fluid can be injected into port 286H, and flow through the lumen of tube 285H, into the lumen 205 of the hub 210 and shaft 220 of the probe 200, and out from the opening from the lumen 205 in the bevel 221. The tube 285H can have a length selected from the range 0 to 30 cm, or longer. Probe 200 includes an integral connection 284H to electrical signal generator 270. The hub closure 282H physically fixes both the generator connection 284H and the shaft 287H and creates a fluid seal around the wire 284H and shaft 287H. The portions of the wire 284H and the shaft 287H within the hub 110, probe shaft 220, and hub closure 282H are shown as dotted and dashed lines, respectively. The wire 284H can have a length selected from the range 30 cm to 3 meters, or longer. Connection 284H includes an insulated wire that conducts electrical signals from the generator electrical output pole labeled "+" through the proximal hub enclosure 282H and to metal shaft 287H within the probe lumen 205 via junction 283H. Metal shaft 287H can be a stainless steel rod or tube, or a rod or tube containing another conductive material, such as nitinol. The metal shaft 287H contacts the inner wall of metal shaft 220 at point 289H and thereby conducts electrical signals from the + pole of the generator 270 to the active tip 201 of the probe. Connection 284H conducts temperature signals to the generator 270 that are measured by a temperature sensor positioned at the distal end 281H of shaft 287H within the lumen 205 of probe 200. The generator 270 can display the temperature signal to the user of the generator 270, and can use the temperature signal to control the electrical signal applied across the generator output poles + and − to suit clinical objectives, such as control of temperature at the probe active tip 201. Reference plate electrode 260 is positioned in contact with the external surface of the tissue 290 and connected to the generator terminal labeled "−" via wire 265 in order to carry current flowing through body 290 from active tip 201 of the probe connected to the "+" terminal of the generator 270. The system presented in FIG. 2H is one embodiment of an adaptation of probe 200 to form a unitized electrode. Other embodiments are possible, such as directly connecting the generator wire 284H to the shaft 220, omitting the injection port 286H and tubing 285H, and/or omitting the temperature sensor 281H within the active tip 201. In some embodiments, the system in FIG. 2H is adapted for RF ablation, the adapted probe 200 is an RF injection electrode, and the generator 270 is an RF generator. In some embodiments, the generator can produce a nerve-stimulation signal, and the adapted probe 200 in FIG. 2H can be used for stimulation-guided nerve blocks and/or ablation. In some embodiments, the probe 100 of FIG. 1 can be adapted in a manner similar to the adaptable of probe 200 in FIG. 2H to form a tissue-piercing, temperature-monitoring, injection electrode.

Figure 3:
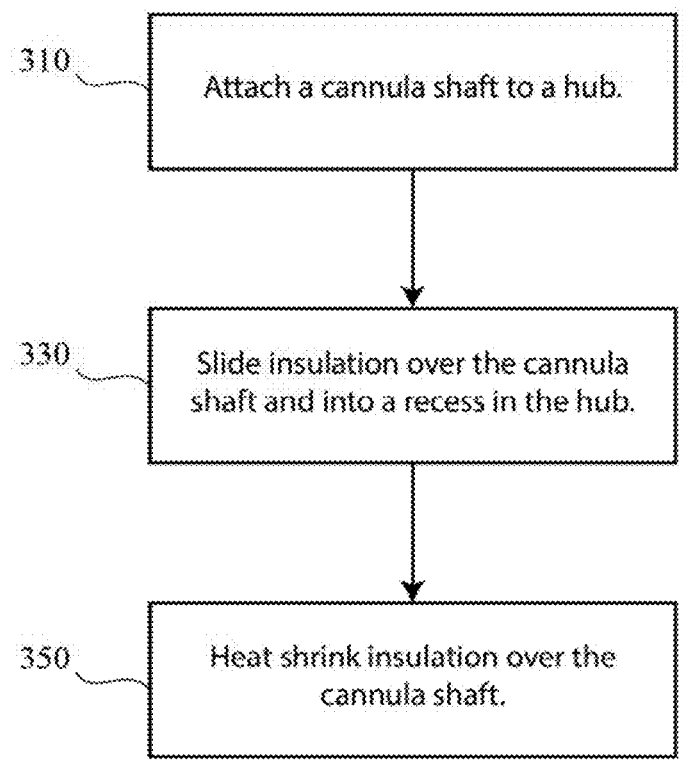
FIG. 3 is a flow chart that shows a method of constructing a medical probe comprising: attaching a shaft to a hub, and applying coating over the shaft and inside a recess in the hub.

Referring now to FIG. 3, one embodiment of a method for assembly of a coated medical probe presented as a flow chart, in accordance with several aspects of the present invention. In one aspect, FIG. 3 relates to the robust coating of a medical probe. In one aspect, FIG. 3 relates to the robust electrical insulation of a medical probe. In one aspect, FIG. 3 relates to the efficient manufacture of a medical electrode. In one aspect, FIG. 3 relates to construction of an RF cannula. In one aspect, FIG. 3 relates to construction of an RF electrode. In one aspect, FIG. 3 relates to robust and efficient application of heat-shrink tubing to a needle, such as an RF cannula, RF electrode, nerve-stimulation needle, muscle-stimulation needle, or medical recording electrode.

In the first step 310, a medical cannula (such as needle 150) is constructed by attaching an elongated shaft (such as shaft 120) to a hub (such as hub 110). The attaching can comprise molding the hub to the shaft, gluing the hub to shaft, pressing the hub into the shaft, or otherwise fixedly attaching the hub to the shaft. The next step 330 comprises sliding electrically-insulative heat-shrink tubing (such as insulation 130) over the shaft and into a recess is the hub (such as hub recess 111). The next step 350 comprises heating the tubing, for example by means of a heat gun set to a temperature sufficient to recover the diameter of the heat shrink tubing, so that the insulation is tight to the cannula shaft and one end of the insulation remains shrouded in the recess (for example, as shown by probe 100 in FIG. 1B). One advantage of the process shown in FIG. 3 is that a cannula having a shaft and a hub can be constructed in a first process 310 without concern for the durability of the ultimate insulation of the cannula, which is only applied afterward in a second process 330. For example, the process of constructing a bare cannula (such as needle 150) in step 310 can include temperatures, manipulation, chemicals, environmental conditions, and other process that might risk the integrity of the cannula shaft insulation. For example, in step 310, the process of grasping the cannula shaft could be damaging to electrical insulation already applied to the cannula shaft. For example, in step 310, the heat required to mold the hub onto the shaft could melt insulation if already applied to the shaft. Another advantage of the process of FIG. 3 is that the cannula can be produced in a generic mass-manufacturing process, and then the produced cannula can be divided into different finishing processes, of which processes 330 and 350 are only one example. In some embodiments, the probe 100 shown in FIG. 1 can be produced by means of the process in FIG. 3.

In other embodiments of the process of FIG. 3, the insulation can take other forms, such as non-heat-shrink tubing that is fixed to the cannula by mechanical interference and/or glue. In another embodiment, the insulation can be painted on or sprayed onto the cannula shaft in step 330, and the paint can dry or be heat cured in step 350. In some embodiments, the process of FIG. 3 can be adapted to applying a coating a solid probe, the coating being either electrically-insulative or non-electrically-insulative. In some embodiments, the process of FIG. 3 can be adapted to applying insulating a medical electrode. In some embodiments, the process of FIG. 3 can be adapted to applying insulating ablation probe, such as an RF cannula or an RF electrode. In some embodiments, the insulation can be a generic coating applied to the cannula to suit a non-electrical objective.

Figure 4:
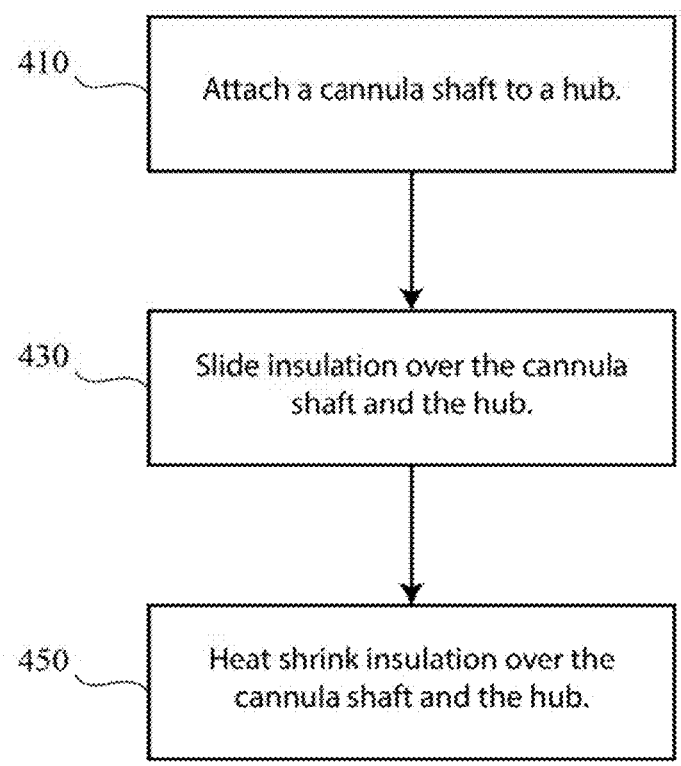
FIG. 4 is a flow chart that shows a method of constructing a medical probe medical probe comprising: attaching a shaft to a hub, and applying electrical insulation over both the shaft and a protrusion from the hub onto the shaft.

Referring now to FIG. 4, one embodiment of a method for assembly of an coated medical probe presented as a flow chart, in accordance with several aspects of the present invention. In one aspect, FIG. 4 relates to the robust coating of a medical probe. In one aspect, FIG. 4 relates to the robust electrical insulation of a medical probe. In one aspect, FIG. 4 relates to the efficient manufacture of a medical electrode. In one aspect, FIG. 4 relates to construction of an RF cannula. In one aspect, FIG. 4 relates to construction of an RF electrode. In one aspect, FIG. 4 relates to robust and efficient application of heat-shrink tubing to a needle, such as an RF cannula, RF electrode, nerve-stimulation needle, muscle-stimulation needle, or medical recording electrode.

In the first step 410, a medical cannula (such as needle 250) is constructed by attaching an elongated shaft (such as shaft 220) to a hub (such as hub 210). The attaching can comprise molding the hub to the shaft, gluing the hub to shaft, pressing the hub into the shaft, or otherwise fixedly attaching the hub to the shaft. The next step 430 comprises sliding electrically-insulative heat-shrink tubing (such as insulation 230) over the shaft and over a portion of the hub (such as protrusion 211). The next step 450 comprises heating the tubing, for example by means of a heat gun set to a temperature sufficient to recover the heat shrink tubing diameter, so that the insulation is tight to the cannula shaft and a portion of the hub (for example, as shown by 200 in FIG. 2B). One advantage of the process shown in FIG. 4 is that a cannula having a shaft and a hub can be constructed in a first process 410 without concern for the durability of the ultimate insulation of the cannula, which is only afterward applied in a second process 430. For example, the process of constructing a bare cannula (such as needle 250) in step 410 can include temperatures, manipulation, chemicals, environmental conditions, and other process that might risk the integrity of the cannula shaft insulation. For example, in step 410, the process of grasping the cannula shaft could be damaging to electrical insulation already applied to the cannula shaft. For example, in step 410, the heat required to mold the hub onto the shaft could melt insulation if already applied to the shaft. Another advantage of the process of FIG. 4 is that the cannula can be produced in a generic mass-manufacturing process, and then the produced cannula can be divided into different finishing processes, of which processes 430 and 450 are only one example. In some embodiments, the probe 200 shown in FIG. 2 can be produced by means of the process in FIG. 4.

In other embodiments of the process of FIG. 4, the insulation can take other forms, such as non-heat-shrink tubing that is fixed to the cannula by mechanical interference and/or glue. In another embodiment, the insulation can be painted on or sprayed onto the cannula shaft and a portion of the hub in step 430, and the paint can dry, be melted, or be heat cured in step 450. In some embodiments, the process of FIG. 4 can be adapted to applying coating a solid probe, the coating being electrically-insulative or non-electrically-insulative. In some embodiments, the process of FIG. 4 can be adapted to applying insulating a medical electrode. In some embodiments, the process of FIG. 4 can be adapted to applying insulating an ablation probe, such as an RF cannula or an RF electrode. In some embodiments, the insulation can be a generic coating applied to the cannula to suit a non-electrical objective.

Each of the probes 100 and 200 can be adapted to function as a radiofrequency cannula (examples of which include the Cosman CC cannula and the Cosman RFK cannula). Each of the probes 100 and 200 can be adapted to function as a tissue-piercing, radiofrequency, injection electrode (one example of which is the Cosman CR electrode). Each of the probes 100 and 200 can be adapted to function as a temperature-monitoring, tissue-piercing, radiofrequency, injection electrode (one example of which is Cosman CU electrode). Each of the probes 100 and 200 can be adapted to function as a tissue-piercing, nerve-stimulating, injection needle (one example of which is the Cosman CP electrode). Each of the probes 100 and 200 can be adapted to function as an electrode, needle, injection needle, injection electrode, RF electrode, RF cannula, cooled RF electrode, MW ablation antennae, non-cooled RF electrode, stimulation electrode, nerve-stimulation probe, muscle stimulation probe, or an electrical measurement probe. Each of the probes 100 and 200 can be adapted for application of monopolar signals, bipolar signals, multi-polar signals, and combinations and sequences thereof, in concert with other probes. Each of the probes 100 and 200 can be adapted to have multiple, electrically-isolated electrical contacts, for example, by nesting additional insulated needle shafts within the shown needle shafts 120 and 220. Each of the probes 100 and 200 can adapted for tissue ablation, and can be used with other probes ablation probes that produce heat lesions sequentially or at the same time. Each of the probes 100 and 200 can be adapted for tissue ablation in a wide variety of clinical contexts including tissue coagulation, pain management, tumor ablation, cardiac ablation, tissue devascularization, open surgical procedures, percutaneous surgical procedures, laparoscopic surgical procedures, facet denervation, SIJ denervation, pulsed RF neuromodulation, pulsed RF lesioning, preparation of collapsed bone for injection of bone cement, lesioning of intravertebral nerves, lesion of intra-bone structures. Each of the probes 100 and 200 can be adapted for tissue ablation in all parts of the human body including the spine, bone, spinal nerve, peripheral nerve, knee nerve, hip nerve, shoulder nerve, foot nerve, hand nerve, carpel tunnel, sympathetic nerve, trigeminal nerve, medial branch nerve, sacral lateral branch nerve, brain, heart, liver, kidney, lung, pancreas, prostate, adrenal gland, thyroid, gall bladder, vertebral body, intervertevral nerve, basivertebral nerve, an intervertebral disc, nerve in an intervertebral disc, posterior annulus of an intervertebral disc, nucleus of the intervertebral disc, muscle, osteoid osteoma.

A number of embodiments of the invention have been described. Nevertheless, it will be understood that various modifications may be made without departing from the spirit and scope of the invention. Accordingly, other embodiments are within the scope of the following claims. What we claim are the following:

What is claimed is:

1. A probe including a needle and a coating having a proximal end and a distal end, the needle including an elongated shaft and a hub, the shaft having a proximal end and a distal end, the distal end of the shaft being configured for insertion into bodily tissue, the hub being fixedly attached to the proximal end of the shaft and including a recess between the hub and the shaft, the coating covering at least a part of the shaft, and the proximal end of the coating being positioned within the recess, wherein the coating is heat-shrink tubing, and wherein a proximal end of the shaft within the recess is uncovered by the coating.

2. The probe of claim 1 wherein the hub includes a port that connects to a lumen through the shaft.

3. The probe of claim 1 wherein the shaft is tissue-piercing.

4. The probe of claim 1 wherein the hub is electrically insulative, the coating is electrically insulative, the shaft is electrically-conductive and includes an active tip, the active tip being a portion of the distal end of the shaft that is not covered by the coating.

5. The probe of claim 4 wherein the probe is configured for radiofrequency tissue ablation.

6. The probe of claim 4 wherein the hub includes a port that connects to a lumen through the shaft, the port and lumen are configured to admit an electrode, and the electrode is configured to electrify the active tip when the electrode is positioned within the lumen.

7. The probe of claim 4 and further including an integral connection to an electrical signal generator through which an electrical signal from the electrical signal generator is conducted to the active tip.

8. The probe of claim 4 further including a fluid line and a generator cable; the fluid line including a port and a flexible tube connecting the port to the hub and to a lumen through the shaft; the port, tube, and lumen being configured for injection of fluids into the port, through the tube, through the shaft, and out from an opening in the shaft; the generator cable being configured to conduct an electrical signal from an electrical signal generator to the active tip.

9. The probe of claim 8 and further including a temperature sensor configured to measure the temperature at the active tip, the electrical signal generator being a radiofrequency generator configured to perform radiofrequency tissue ablation, the generator cable configured to conduct a temperature-measurement signal from the temperature sensor to the radio frequency generator.

10. The probe of claim 1, wherein the heat-shrink tubing contracts both longitudinally and radially upon heating, wherein the probe is made by a process that comprises sliding the heat-shrink tubing over the shaft and into the recess, and applying heat to the heat-shrink tubing to shrink the heat-shrink tubing onto the shaft and within the recess in the hub, and wherein a longitudinal dimension of the recess is sized such that when the coating is fully inserted into the recess and shrinking heat is applied, a proximal end of the heat-shrink tubing remains within the recess.

11. The probe of claim 1, wherein the heat-shrink tubing is selected from a material selected from PTFE, FEP, PET and polyolefin.

12. A method for constructing a coated probe comprising: assembling a shaft and hub, and applying a coating over the shaft and within a recess in the hub, wherein the coating is heat-shrink tubing, and wherein applying the coating over the shaft and within the recess in the hub comprises sliding the heat-shrink tubing over the shaft and into the recess, and applying heat to the heat-shrink tubing to shrink the coating onto the shaft and within the recess in the hub.

13. The method of claim 12, wherein the heat-shrink tubing contracts both longitudinally and radially upon heating, and wherein a longitudinal dimension of the recess is sized such that when the coating is fully inserted into the recess and shrinking heat is applied, a proximal end of the heat-shrink tubing remains within the recess when applying heat to the heat-shrink tubing.

14. The method of claim 12, wherein the heat-shrink tubing is selected from a material selected from PTFE, FEP, PET and polyolefin.

* * * * *